United States Patent [19]

Staton et al.

[11] Patent Number: 5,801,214
[45] Date of Patent: Sep. 1, 1998

[54] DENTURE RETAINING COMPOSITION

[75] Inventors: John Alexander Staton, Kingsgrove; Luke Thomas, Dural, both of Australia

[73] Assignee: Confi-Dent Pty Limited, New South Wales, Australia

[21] Appl. No.: 665,197

[22] Filed: Jun. 14, 1996

[30] Foreign Application Priority Data

Jun. 15, 1995 [AU] Australia .................. PN3558

[51] Int. Cl.$^6$ .............. A61K 6/08; A61K 6/097; C08L 5/04; C08L 5/00
[52] U.S. Cl. ............ 523/118; 523/120; 524/28; 524/55; 524/267; 524/268; 524/386
[58] Field of Search .............. 523/120, 118; 524/28, 55, 267, 268, 386

[56] References Cited

U.S. PATENT DOCUMENTS

| | | | |
|---|---|---|---|
| 3,575,915 | 4/1971 | Novak et al. | 524/390 |
| 4,474,902 | 10/1984 | Dhabhar et al. | 523/120 |
| 5,011,868 | 4/1991 | Keegan | 523/120 |
| 5,422,112 | 6/1995 | Williams | 424/401 |
| 5,567,426 | 10/1996 | Nadaud et al. | 424/401 |

FOREIGN PATENT DOCUMENTS

| | | |
|---|---|---|
| 0 026 332 | 8/1980 | European Pat. Off. . |
| 0 073 850 | 9/1981 | European Pat. Off. . |
| 65210 | 3/1993 | Japan . |

*Primary Examiner*—Peter A. Szekely
*Attorney, Agent, or Firm*—McDermott, Will & Emery

[57] ABSTRACT

A composition for retaining dentures in the mouth of a denture wearer including 5–8% w/w of an hydrophilic gelling agent, 2–7% w/w of a thickening agent, 5–20% w/w of ail agent that imparts water resistance to the composition, 0.2–5% w/w of humectant(s) and the balance being water, the composition being formable into a viscous hydrophobic film in use. A method of retaining dentures in the mouth of a denture wearer by applying to the denture or the mouth tissue the composition and placing the denture into position in the mouth in a manner such that the composition substantially forms a seal between the mouth tissue and the denture to thereby assist in the retention of the denture.

9 Claims, No Drawings

5,801,214

DENTURE RETAINING COMPOSITION

TECHNICAL FIELD

The present invention relates to compositions and methods for holding dentures in position in the mouth of a denture wearer.

BACKGROUND OF THE INVENTION

The methods currently in use for positioning and holding dentures in the mouth are based primarily on applying adhesive compositions to the dentures prior to insertion. Such adhesive compositions come in the form of adhesive creams or adhesive powders and utilise the stickiness of the compositions to hold the dentures in position.

The denture adhesives available at present have many disadvantages. One of the major disadvantages is in the difficulty in the application of the material to the denture prior to insertion. The adhesives are often quite messy and are awkward to apply and use. This problem is particularly significant taking into account the majority of denture wearers are elderly. The dexterity, coordination and eyesight are often impaired in the elderly and this exacerbates the difficulty in applying present denture adhesives to their dentures. This is particularly relevant with the powder adhesives as this material has to be sprinkled onto the plate of the denture before insertion. This can be a difficult task for the elderly and often results in considerable waste of the material due to the failure to apply the correct amount to the denture surface.

Furthermore, the texture of the denture adhesives are often sandy or gritty and may cause irritation to the gum and surrounding tissue when used for prolonged periods. The majority of the denture adhesives available also have a strong taste and this can often be offensive to the wearer.

As the adhesive materials have the tendency to set hard in order for them to achieve their desired function in use, there is a real problem of removing the hard material from the dentures, the mouth tissue and remaining teeth in the mouth after use. If the denture adhesives are not removed completely after use, there is a gradual build-up of the adhesives on the dentures which causes further problems of fit and comfort to the wearer. Ultimately, this build-up may cause irritation to the dental tissues resulting in severe discomfort and pain. There is also the real risk of damaging the dentures during harsh techniques often required to remove the adhesive build-up. Again, taking into account the proportion of the elderly population that wear dentures, this removal process may pose a serious problem to them.

The presently available materials normally act for only up to 12 hours of use. If the material is not applied carefully to the dentures the appearance of excess material on the dentures is often unsightly. The materials are often applied liberally on the plate of the dentures prior to insertion and any excess is extruded from out between the dental tissue and the plate of the denture when used. The adhesive nature of the material often results in the covering of the teeth component of the denture with unsightly build-up.

The main indication of using the adhesives presently available is for loose fitting dentures. There are no suitable materials available at present for normal fitting dentures that will assist in their retention in the mouth for prolonged periods.

A further disadvantage of denture adhesives presently available is that saliva of the denture wearer is required as a lubricant between the oral tissues and the denture and/or as a diluent for the adhesive. Denture wearers that have reduced saliva production resulting from conditions such as diabetes are unable to use successfully these denture adhesives. There is a need for a denture retaining composition that does not rely to any great extent on the saliva production of the denture wearer for its action.

The alternative to the denture adhesives presently available are cushions adapted to be inserted in very loose dentures to fill the gap between the denture and the tissue of the mouth. These cushions are also difficult to apply to the dentures and have a rough texture that may cause irritation to the surrounding dental tissue. Furthermore, a real disadvantage of the denture cushions is that they absorb food and odours and therefore are a source of oral odour for the wearer. Additionally, they may pose a health risk due to the growth of bacteria from the mouth. Consequently the denture cushions should only be used for a short period of time, approximately six hours.

The present inventors have realised that there is a need for a better denture retaining composition which when in use will address many of the problems of the denture retaining materials presently available.

BRIEF SUMMARY OF THE INVENTION

Accordingly, in a first aspect the present invention consists in a composition for retaining dentures in the mouth of a denture wearer, the composition comprising:

(a) hydrophilic gelling agent;
(b) thickening agent;
(c) agent that imparts water resistance to the composition;
(d) humectant(s); and
(e) the balance being water;

the composition being formable into a viscous hydrophobic film in use.

In a preferred embodiment of the first aspect of the present invention, the composition comprises:

(a) 5–8% w/w of an hydrophilic gelling agent;
(b) 2–7% w/w of a thickening agent;
(c) 5–20% w/w of a water resistance imparting agent;
(d) 0.2–5% w/w of humectant(s); and
(e) the balance being water.

In a further preferred embodiment of the first aspect of the present invention, the composition comprises:

(a) 7% w/w of an hydrophilic gelling agent;
(b) 4% w/w of a thickening agent;
(c) 10% w/w of a water resistance imparting agent;
(d) 1% humectant(s); and
(e) the balance being water.

When the composition is in the form of an emulsion, the composition optionally includes an emulsifier stabilising agent or agents.

In a still further preferred embodiment of the first aspect of the present invention, the hydrophilic gelling agent is alginate or xanthan gum. One form of xanthan gum suitable for the present invention is sold under the trade name "KELTROL" by Merck & Co, but other similar agents may be used for the present invention.

The thickening agents for the present invention may be in the form of a polyacrylamide composition together with non-ionic surfactants. A suitable thickening agent for the present invention when the composition is in the form of an emulsion is sold under the trade name "SEPIGEL 305" by Bleakley Fine Chemicals, Australia. According to the manufacturer "SEPIGEL 305" is a polymer substance designated as: polyacrylamide (and) $C_{13-14}$ isoparafin (and) LAURETH-7 (an alkyl poly(ethyleneoxide) consisting of a lauryl group and seven repeating ethyleneoxide units). It will be appreciated by persons skilled in the art, however, that other thickening agents may also be used for the present invention.

The water resistance imparting agent is preferably a water resistant liquid silicone. A suitable liquid silicone suitable for the present invention is sold under the trade name "DOW CORNING 200" fluid but other similar carrying agents are also suitable for the present invention. The function of the water resistance imparting agent is to provide to the composition resistance to dispersion by normal salivary processes when in use.

The humectants suitable for the present invention include propylene glycol or similar compounds and the water is preferably purified water.

The composition of the present invention may further include dye materials and preservatives known to the art. These further additives may impart colour and taste to the composition, promote the shelf life of the composition and prevent microbial growth.

The composition of the present invention consists of a combination of hydrophilic and hydrophobic gelling agents together with vehicles or carriers which are adapted to form a viscous hydrophobic film which is cosmetically acceptable for use in the mouth.

It will be appreciated by one skilled in the art that the composition can have any viscosity prior to use but the composition should form a viscous hydrophobic film in situ so as to substantially form a seal between the denture and the mouth tissue.

The composition of the present invention is not an adhesive agent but acts in use as a sealing agent that substantially promotes a seal between the dentures and the dental tissue when the dentures are inserted in the mouth. Furthermore, as the composition of the present invention retains its viscous state and is hydrophobic, after use it can be removed relatively easily as it does not adhere to hard tissues in the form of natural teeth, soft tissues in the form of gums and mucosa and the denture base. After removing the dentures, the denture retaining composition is removed from the denture base by wiping with a tissue or the like. The composition does not set and therefore there is little problem of accumulation of the composition on the dentures due to any difficulty in removal as experienced with the dental adhesives in use at present.

In a second aspect, the present invention consists in a method of retaining dentures in the mouth of a denture wearer comprising the following steps:

(a) applying to the denture or the mouth tissue a composition comprising 5–8% w/w of an hydrophilic gelling agent, 2–7% w/w of a thickening agent, 5–20% w/w of an agent that imparts water resistance to the composition, 0.2–5% w/w of humectant(s) and the balance being water, the composition being formable into a viscous hydrophobic film in use; and (b) placing the denture into position in the mouth in a manner such that the composition substantially forms a seal between the mouth tissue and the denture to thereby assist in the retention of the denture.

When the composition is in the form of an emulsion, the composition optionally includes an emulsifier stabilising agent(s).

In a preferred embodiment of the second aspect of the present invention, the composition is applied to the denture and, more preferably, the composition is applied around the borders of the denture so as to ensure that a substantial seal is made between the mouth tissue and the denture when the denture is inserted in the mouth.

DETAILED DESCRIPTION OF THE INVENTION

In order that the present invention may be more clearly understood, a preferred form thereof will be described with reference to the following example.

One example of the composition of the present invention in the form of an emulsion is given in Table I. In this example, the hydrophilic gelling agent is xanthan gum sold under the trade name "KELTROL F" by Merck & Co. The thickening and stabilising agent is in the form of a polyacrylamide composition together with non-ionic emulsifiers and is sold under the trade name "SEPIGEL 305" by Bleakley Fine Chemicals. The water resistance imparting agent is a water resistant liquid silicone sold under the trade name "DOW CORNING 200" liquid fluid. The humectant is propylene glycol. The composition further comprises a dye and preservatives.

TABLE I

| Material | % | gm | Supplier |
|---|---|---|---|
| Keltrol F | 7.00 | 70.000 | Kelco Australia |
| Sepigel 305 | 4.000 | 40.000 | Bleakley Fine Chemical |
| Dow 200 Fluid - simethicone | 10.000 | 100.000 | Dow |
| propyl hydroxy-benzoate | 0.160 | 1.600 | Bronson & Jacobs |
| methyl hydroxy-benzoate | 0.040 | 0.400 | Bronson & Jacobs |
| F D & C Red No 40 (1% solution) | 0.060 | 0.600 | Hodgsons Dye Agencies |
| Propylene glycol | 1.000 | 10.000 | Bronson & Jacobs |
| Purified Water | 77.740 | 777.400 | |

The composition is produced by dissolving propyl and methyl hydroxybenzolate in propylene glycol, dispersing the "KELTROL" in water with slow stirring over a long period of time until the mixture is lump free and dispersing the "SEPIGEL" in simethicone with slow stirring. The "KELTROL" in water solution is then combined with the dissolved propylene and methyl hydroxybenzolate solution and combining the "SEPIGEL" solution with the remaining ingredients and finally adding the red dye.

The composition according to the present invention is in the form of a viscous hydrophobic material having a viscosity of about 500,000 cP. The composition is formulated so as to not wash away by the normal salivary process when in use. It is preferred but not essential that the denture retaining composition is applied in a continuous line around the inner borders of the denture so as to promote a substantial seal between the denture and the dental tissue in use. It will be appreciated, however, that any means of applying the composition prior to insertion of the denture would be acceptable.

The denture retaining composition of the present invention is suitable for all denture wearers on a regular or daily basis. In denture wearers, the oral tissues and mucosa by their nature under go constant dimensional change. This results in most denture wearers regularly suffering from problems ranging from mild irritation or discomfort to lack of retention from ill-fitting dentures. In addition, newly fitted dentures after tooth extraction often cause severe discomfort to the patient. The present inventors have developed a denture retaining composition that is particularly suitable to provide relief from these conditions and problems.

In order to test and demonstrate the suitability of the present composition, an in vivo test was carried out with a male volunteer. The volunteer was selected as he wears dentures comprising full maxillary and full mandibular dentures having poor retention. The composition of the example was applied to the dentures and then the dentures were inserted at 12.50 am. The dentures were finally removed at 6.00 pm. on the following day, representing a usage duration of 29 hours.

Table II shows the activities of the volunteer while wearing the dentures during this test period. It can be seen from Table II that the volunteer carried out normal eating and drinking activities throughout the test period and loss of retention was recorded after a period of 29 hours of use.

TABLE II

| Time Composition Applied | Comments | Acitvity |
|---|---|---|
| 1.15 pm | (No discharge or loss of retention) | Egg sandwiches |
| 3.15 pm | | Hot cup of tea |
| 5.20 pm | | Two orange cream biscuits |
| 6.20 pm | | Sausages (large) peas & mashed potatoes |
| 10.15 pm | | Hot cup of tea |
| 10.30 pm | Upper denture removed, checked, reinserted | |
| 7.00 am | | Toast & Weetbix |
| 12.30 pm | | Sandwiches |
| 1.00 pm | | Hot cup of tea |
| 6.00 pm | Loss of retention | |

During the test time of 29 hours, the volunteer felt as though the dentures were "a part of him". The volunteer was questioned at half hour intervals and at no stage during the test period did the dentures lose retention. The volunteer was not aware of any taste or discharge at any time. To further test the effectiveness of the composition, the dentures were removed twice during the 29 hour period and then reinserted without any loss of retention. At no stage was the composition reapplied during the times when the dentures were removed.

The volunteer suffers from violent coughing which further exacerbates the problem of retaining dentures in the mouth. The test demonstrated that the composition of the present invention is suitable to retain dentures in the mouth in a controlled and user-friendly manner. When the present denture retaining composition is in use, it is not detectable and therefore promotes further confidence in the wearers of dentures.

Seven additional subjects were studied for their reaction to the use of a denture retaining composition according to the present invention. The results of this study are summarised in Table III. It can be seen from this table that in all subjects the composition improved the fit of their dentures. Furthermore, in many of the subjects there was also a marked improvement in comfort of wearing their dentures.

An important aspect of the composition of the present invention is that it is adapted so as to be able to substantially promote a seal between the mouth tissue and the dentures in use. The composition is suitable for use not only with loosely fitting dentures but with all dentures to improve comfort. As the composition does not rely or depend on saliva production of the wearer as it has inherent lubricating characteristics, it is suitable for denture wearers that may have reduced saliva production due to old age or medical conditions like diabetes. The composition is not an adhesive and therefore reflects a move away from the traditional compositions and methods of retaining dentures.

TABLE III

| Case Study No | Denture | Time of Insertion (hours) | Comments |
|---|---|---|---|
| 1 | Full maxillary | 29 | Improved denture fit; |
|   | Full mandibular | 29 | Improved retention |
| 2 | Full maxillary | 31 | Comfortable; Relief from |
|   | Full mandibular | 7.5 | denture movement |
| 3 | Full maxillary | 4 | Improved denture fit; |
|   | Full mandibular | 4 | Prevented denture movement |
| 4 | Full maxillary | 4 | Improved denture fit; |
|   | Full mandibular | 4 | Comfortable |
| 5 | Full maxillary | 4 | Improved denture fit |
| 6 | Full maxillary | 6 | Improved denture fit; |
| 7 | Full mandibular | 4.5 | Improved denture fit; |
| 8 | Full maxillary | 23.8 | Improved denture fit; |
|   | Full mandibular | 23.8 | |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A denture-retaining composition for retaining dentures in the mouth of a denture wearer, the composition consisting essentially of:

(a) 5–8% w/w of an hydrophilic gelling agent;
   (b) 2–7% w/w of a thickening agent;
   (c) 5–20% w/w of an agent that imparts water resistance to the composition:
   (d) 0.2–5% w/w of humectant(s); and
   (e) the balance being water;

the composition being formable into a viscous hydrophobic film in use so as to form a seal between a denture and mouth tissue.

2. The composition according to claim 1 comprising:

(a) 7% w/w of the hydrophilic gelling agent;
   (b) 4% w/w of the thickening agent;
   (c) 10% w/w of the water resistance imparting agent;
   (d) 1% w/w humectant(s); and
   (e) the balance being water.

3. The composition according to claim 1 wherein the hydrophilic gelling agent is alginate or xanthan gum.

4. The composition according to claim 1 wherein the thickening agent is in the form of a polyacrylamide composition together with non-ionic surfactants.

5. The composition according to claim 1 wherein the water resistance imparting agent is a water resistant liquid silicone.

6. The composition according to claim 1 wherein the humectants include propylene glycol and the water is purified water.

7. The composition according to claim 1 further comprising an emulsifier stabilising agent.

8. The composition according to claim 1 further comprising dye materials.

9. The composition according to claim 1 further comprising preservatives.

* * * * *